United States Patent [19]

Schmitz-Josten et al.

[11] 4,323,696

[45] Apr. 6, 1982

[54] (METH)ACRYLIC ACID ESTERS OF TRICYCLIC DECANEDIOLS CONTAINING ETHER GROUPS

[75] Inventors: Robert Schmitz-Josten, Cologne, Fed. Rep. of Germany; Manfred Dietrich, New Martinsville, W. Va.; Bruno Bömer, Leverkusen, Fed. Rep. of Germany

[73] Assignee: Bayer Aktiengesellschaft, Leverkusen, Fed. Rep. of Germany

[21] Appl. No.: 174,332

[22] Filed: Aug. 1, 1980

[30] Foreign Application Priority Data

Aug. 7, 1979 [DE] Fed. Rep. of Germany ....... 2931925

[51] Int. Cl.$^3$ .............................................. C07C 69/54
[52] U.S. Cl. ..................................... 560/220; 526/282
[58] Field of Search .......................... 560/220; 433/168

[56] References Cited

U.S. PATENT DOCUMENTS 3,586,526 6/1971 Arnoff et al. ....................... 560/221

4,131,729 12/1978 Schmitt et al. ....................... 526/282

FOREIGN PATENT DOCUMENTS 2714538 10/1978 Fed. Rep. of Germany ...... 560/220

OTHER PUBLICATIONS

Jandourck, Hana, *Chemical Abstracts,* vol. 81 (1974) #171,512v.

*Primary Examiner*—Natalie Trousof
*Assistant Examiner*—L. Hendriksen
*Attorney, Agent, or Firm*—Sprung, Felfe, Horn, Lynch & Kramer

[57] ABSTRACT

The invention relates to (meth)acrylic acid esters of compounds of Formula (I) as defined infra and methods for their preparation. The esters formed can be used to provide dental repair material and also to provide adhesive or sealing agents. In addition, the invention includes a process for preparing compositions which harden in the absence of oxygen by admixing a compound of the invention with an initiator.

8 Claims, No Drawings

(METH)ACRYLIC ACID ESTERS OF TRICYCLIC DECANEDIOLS CONTAINING ETHER GROUPS

The present invention relates to certain new acrylic acid esters and methacrylic acid esters of tricyclic decanediols containing ether groups.

The diacrylates and dimethacrylates of di-(hydroxymethyl)-tricyclo[5.2.1.0$^{2.6}$]-decanes are known from DE-OS (German Published Specification) No. 2,200,021. The use of these esters of the preparation of dental compositions is described in DE-OS (German Published Specification) No. 2,816,823. The shinkage of polymerisation and the flexural strength of these esters are not satisfactory for the given intended use.

According to the present invention there are provided compounds which are (meth)acrylic acid esters of tricyclic decanediols, containing ether groups, of the formula

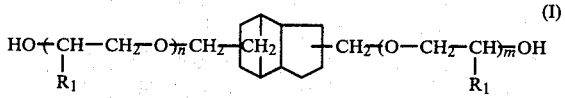

in which

R$_1$ represents a hydrogen atom, a methyl group or an ethyl group, preferably a hydrogen atom or a methyl group, and n+m represents an integer from 1 to 10.

The esters of the present invention are outstandingly suitable for the preparation of dental compositions.

According to the present invention there is further provided a process for the production of compounds of the invention in which each mole of a 3,8-, 3,9- or 4,8-di-(hydroxymethyl)-tricyclo-[5.2.1.0$^{2.0}$]-decane or mixture thereof is initially reacted with 1 to 10 moles of an alkylene oxide of the formula

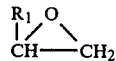

in which R$_1$ has the meaning indicated above, and the compound of the formula (I) thereby formed is converted into its (meth)acrylic acid esters. Particularly preferred alkylene oxides of formula (I) are ethylene oxide and propylene oxide.

The starting materials used for the preparation of the compounds according to the invention are the tricyclo[5.2.1.0.$^{2.6}$]-decanes, containing hydroxymethyl groups in the 3,8-, 3,9- or 4,8-position, of the general formula

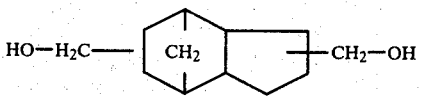

which can be obtained by the Oxo synthesis in a manner which is in itself known, from carbon monoxide and dicyclopentadiene in the presence of cobalt catalysts, with subsequent hydrogenation of the tricyclodecane-dialdehydes formed, a mixture of the isomers being formed. This mixture is called "TCD-DM or Tricyclo-decane-dimethanol".

Each mole of these starting materials is reacted with 1 to 10 moles of a C$_2$ to C$_4$ alkylene oxide (ethylene oxide, propylene oxide or butylene oxide) generally at temperatures of 70° to 150° C. (preferably at 100° to 120° C.) in the presence of basic catalysts to give compounds of the formula (I), the alkylene oxide appropriately being metered in at a rate depending on the rate at which it is consumed. By this reaction mixtures of compounds of the formula I are obtained, the average composition of which depends on the amount of reacted alkylenoxide and corresponds to the meaning of n+m as an integer from 1 to 10.

Alkali metal alcoholates or alkaline earth metal alcoholates, which can also be prepared in situ, are preferably used as the basic catalysts.

In principle, all the reactions which can be used for ester formation can be utilised to prepare the (meth)acrylic acid esters according to the invention from the tricyclic diols of the formula (I). In the simplest case, the tricyclic diol is esterified with (meth)acrylic acid, in particular with the addition of catalysts, it being possible for the water formed to be removed azeotropically from the reaction mixture using solvents. Instead of (meth)acrylic acid, it is, of course, also possible to employ anhydrides or acid halides thereof. Trans-esterification with, for example, the methyl esters or ethyl esters of acrylic acid or methacrylic acid is also possible. In this case, trans-esterification catalysts, such as esters of titanic acid or dibutyl-tin oxide are used. In principle, the tricyclic diols can, of course, also be esterified with a highly volatile acid, for example acetic acid, and trans-esterification with the (meth)acrylic acid ester of a highly volatile alcohol, such as acrylic acid methyl ester or methacrylic acid methyl ester, can then be carried out.

Polymerisation inhibitors should be present in the preparation of the (meth)acrylic acid esters according to the invention in order to avoid premature polymerisation. Suitable inhibitors are the substances known as stabilisers for monomers, such as hydroquinone, dialkylated phenols, quinones, aromatic nitro compounds, phenothiazine or methylene blue. In some cases it is sufficient to ensure that there is an sufficient supply of oxygen to act as a polymerisation inhibitor.

The (meth)acrylic acid esters according to the invention are monomers which can be converted into high-molecular, insoluble compounds by means of known initiators.

As a result of their relatively low viscosity, for example, they are outstandingly suitable for the preparation of highly filled dental repair materials. This use of the materials according to the invention is examplified in copending application Ser. No. 173,945 filed July 30, 1980 . . . (corresponding to German Application No. P 29 31 926.4, filed Aug. 7, 1979). They are furthermore suitable for the preparation of compositions which harden in the absence of oxygen and which are used as adhesives or sealing agents.

Accordingly the present invention further comprises the use of compounds of the present invention for the preparation of a dental repair material and for the preparation of an adhesive or sealing agent. The invention also comprises a process for the preparation of compositions which hardens in the absence of oxygen comprising admixing a compound of the present invention with an initiator.

EXAMPLE A

Instructions for the preparation of the oxyalkylated bis-hydroxy-methyl-tricyclo-[5.2.0.1.$^{2.6}$]-decanes (TCD-DM)

Product A: TCD-DM + 2 mols of ethylene oxide 4,830 g of bishydroxymethyl-tricyclo-[5.2.0.1.$^{2.6}$]-decane (TCD-DM; mixture of the 3,8-, 3,9- or 4,8-isomers) and 600 g of toluene are initially introduced into a stirred autoclave which can be heated and is provided with a device for azeotropic removal of the water, and the air is replaced by nitrogen. 70 g of 50% strength aqueous potassium hydroxide solution are added at 80° C. and 46 g of water is removed from the reaction mixture at 100°–115° C. by azeotropic distillation. 2,170 g of ethylene oxide are then slowly metered in at 100°–115° C. and under 0.4–0.6 bar and the mixture is subsequently stirred at 100°–105° C. for 3 hours. The alkaline reaction product is neutralised with 700 g of water and 245 g of 12.5% strength aqueous sulphuric acid. After adding a filtration auxiliary and an antioxidant, such as 0.05% of 2,6-bis-t-butyl-p-cresol, the water is then distilled off in vacuo at 70° to 90° C. and the salts which have separated out are filtered off, together with the filtration auxiliary. The neutral product thus obtained has a hydroxyl number of 383 and a viscosity $\eta$ 25° C. of 3,550 m Pas.

The following oxyalkylation products of bishydroxymethyl-tricyclo-[5.2.0.1.$^{2.6}$]-decane (TCD-DM) are prepared analogously:

Product B: TCD-DM + 4 mols of ethylene oxide; starting materials: 3,688 g of TCD-DM + 3,312 g of ethylene oxide; OH number: 289; $\eta$ 25° C. = 980 mPas.

Product C: TCD-DM + 8 mols of ethylene oxide; starting materials: 2,504 g of TCD-DM + +,496 g of ethylene oxide; OH number: 187; $\eta$ 25° C. = 480 mPas.

Product D: TCD-DM + 2 mols of propylene oxide; starting materials: 4,398 g of TCD-DM + 2,602 g of propylene oxide; OH number: 341; $\eta$ 25° C. = 5,080 mPas.

Product E: TCD-DM + 4 mols of propylene oxide; starting materials: 3,206 g of TCD-DM + 3,794 g of propylene oxide; OH number: 255; viscosity: $\eta$ 25° C. = 1,330 mPas.

EXAMPLE 1

Methacrylic acid ester of product A 1,460 g of product A, 15 g of methylene blue, 50 g of p-toluenesulphonic acid, 1,150 g of distilled methacrylic acid and 2,000 ml of toluene are heated to the boiling point, whilst bubbling in air. The water which forms is removed by azeotropic distillation. After 8 hours, the splitting off of water has ended. After cooling, the mixture is stirred for 1 hour with 40 g of bleaching earth in order to adsorb the methylene blue and the blue-coloured bleaching earth is filtered off. The filtrate is neutralised with excess sodium carbonate solution until the pH value is 8, and is filtered over a filtration auxiliary, such as cellulose flour. The upper phase is separated off, washed with sodium chloride solution and, after adding a polymerisation inhibitor, concentrated in vacuo until no further toluene is present.

Yield: 1,817 g; saponification number 268 (theory: 262); OH number; 5.6; viscosity; $\eta$ 25° C. = 104 mPas; refractive index: $n_D^{20}$ = 1.4925.

EXAMPLE 2

Methacrylic acid ester of product B

Analogously to Example 1, 1,940 g of product B 15 g of methylene blue, 50 g of p-toluenesulphonic acid, 1,150 g of methacrylic acid and 2,000 ml of toluene are esterified and worked up as described in example 1. Yield: 2,364 g; saponification number: 224 (theory: 216); OH number: 2.3, viscosity: $\eta$ 25° C. = 118 mPas at 13 dynes/cm$^2$; refractive index $n_D^{20}$ = 1.4880.

EXAMPLE 3

Methacrylic acid ester of product C.

Analogously to Example 1, 2,950 g of the methacrylic acid ester with the following characteristics are obtained from 3,000 g of product C: saponification number: 154 (theory: 153); OH number: 5.1; viscosity: $\eta$ 25° C. = 157 mPas; $n_D^{20}$ = 1.4825.

EXAMPLE 4

Methacrylic acid ester of product D 4,051 g of the methacrylic acid ester are obtained from 3,280 g of product D; saponification number: 254; viscosity: $\eta$ 25° C. = 116 mPas; $n_D^{20}$ = 1.4840.

EXAMPLE 5

Methacrylic acid ester of product E 2,918 g of the corresponding methacrylic acid ester are obtained from 2,600 g of product E; saponification number: 197 (theory: 196); OH number: 9.4; viscosity: $\eta$ 25° C. = 143 mPas; refractive index: $n_D^{20}$ = 1.4800.

The corresponding acrylic acid esters are also prepared analogously to Examples 1 to 5 using acrylic acid in place of methacrylic acid.

What is claimed is:

1. Compounds which are acrylic or methacrylic esters of tricyclic decanediols, containing ether groups, of the formula

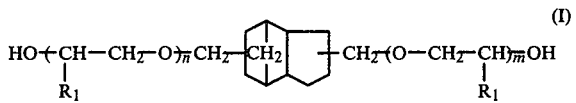

(I)

in which

R$_1$ represents a hydrogen atom, a methyl group or an ethyl group and n + m represents an integer from 1 to 10.

2. Compounds according to claim 1 in which R$_1$ represents a hydrogen atom.

3. Compounds according to claim 1 in which R$_1$ represents a methyl group.

4. Compounds according to claim 1 wherein R$_1$ represents hydrogen and n + m represents the integer 2.

5. Compounds according to claim 1 wherein R$_1$ represents hydrogen and n + m represents the integer 4.

6. Compounds according to claim 1 wherein R$_1$ represents hydrogen and n + m represents the integer 8.

7. Compounds according to claim 1 wherein R$_1$ represents a methyl group and n + m represents the integer 2.

8. Compounds according to claim 1 wherein R$_1$ represents a methyl compound and n + m represents the integer 4.

* * * * *